United States Patent [19]

Matsuno

[11] 4,041,977
[45] Aug. 16, 1977

[54] BREATHING APPARATUS FLOW REGULATOR

[76] Inventor: Takayoshi Matsuno, 1-10 Sumadera-cho, 2-chome, Suma, Kobe, Japan

[21] Appl. No.: 601,536

[22] Filed: Aug. 4, 1975

[51] Int. Cl.$^2$ ............................................. F16K 31/126
[52] U.S. Cl. ................................. 137/494; 128/142.2; 137/DIG. 9; 251/127; 128/210
[58] Field of Search ............... 128/142.2; 137/DIG. 9, 137/494, 504, 614.11; 251/127

[56] References Cited

U.S. PATENT DOCUMENTS

| | | | |
|---|---|---|---|
| 2,893,386 | 7/1959 | Sajeck | 128/142.2 X |
| 3,095,890 | 7/1963 | Cousteau et al. | 137/494 |

Primary Examiner—William R. Cline
Assistant Examiner—H. Jay Spiegel
Attorney, Agent, or Firm—McGlew and Tuttle

[57] ABSTRACT

A device for regulating the flow in a breathing gas apparatus includes a baffle in a housing which is pivotable toward and away from an interior cylindrical wall in order to vary the quantity of air which is directed through a passage defined between the baffle and the wall and into a slot forming an inhalation discharge port which leads to the user of a respiratory device. The baffle may be shifted in the housing by an adjustment means, in the form of a threaded member, to regulate the amount of breathing gas which is directed from the inlet port directly to the slot forming the inhalation discharge port, and the amount which is circulated around the housing when the baffle is moved away from the wall for indirect flow to the uncovered portion of the inhalation discharge slot.

4 Claims, 3 Drawing Figures

BREATHING APPARATUS FLOW REGULATOR

BACKGROUND OF THE INVENTION

1. Field of the Invention

This invention relates in general to flow regulating devices and in particular to a new and useful device for adjusting the air flow supplied to a respirator which includes a baffle plate in a respirator control housing which is movable between a plurality of adjustment positions.

2. Description of the Prior Art

The supplying of breathing air from a compressed air source has had the inherent problems of diverting or regulating the flow of the air, from the high speed flow, as it comes from the source, to a direction and flow comfortable for use in breathing. The underwater regulator devices in common use today provide for a diaphragm which is engaged with a valve mechanism holding the air pressure back. This assembly is adjusted so that as the diver descends in the water the air pressure in the regulator equalling the water pressure on the other side of the diaphragm will hold it motionless and keep the valve closed. As the diver inhales the pressure differential causes the diaphragm to distort toward the air side and causes the valve to open. At this point the high speed air enters the regulator and is blown into the divers mouth through an inhalation discharge port. Through the use of a stationary baffle inside the regulator some comfort has been achieved by diverting or directing the air flow.

SUMMARY OF THE INVENTION

This invention is an improvement over the prior art primarily in respect to the adjustment of the air flow inside a respirator device. The regulator of such a device is provided with a movable baffle which directs the air flow from the point at which it enters the regulator toward the breathing port, or allows the air to flow around the baffle and thus away from the breathing port, when the baffle is manually moved toward and away from the inside wall of the regulator. This interaction with the wall forms a closed or open flow space in which the air travels. By the baffles manual manipulation the diver can chose the most comfortable air flow for himself. This adjustment, not possible in prior art regulators, greatly increases breathing comfort.

An object of this invention is to increase comfort in breathing from respirator devices by regulating the breathing gas flow supplied directly to the breather.

A further object of this invention is to increase the comfort in breathing breathable gases supplied from a high pressure source by regulating its flow direction and speed before it is supplied to the breather.

A still further object of this invention is to provide a respirator control which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there is illustrated a preferred embodiment of the invention.

GENERAL DESCRIPTION OF THE PREFERRED EMBODIMENT

Figure 1:
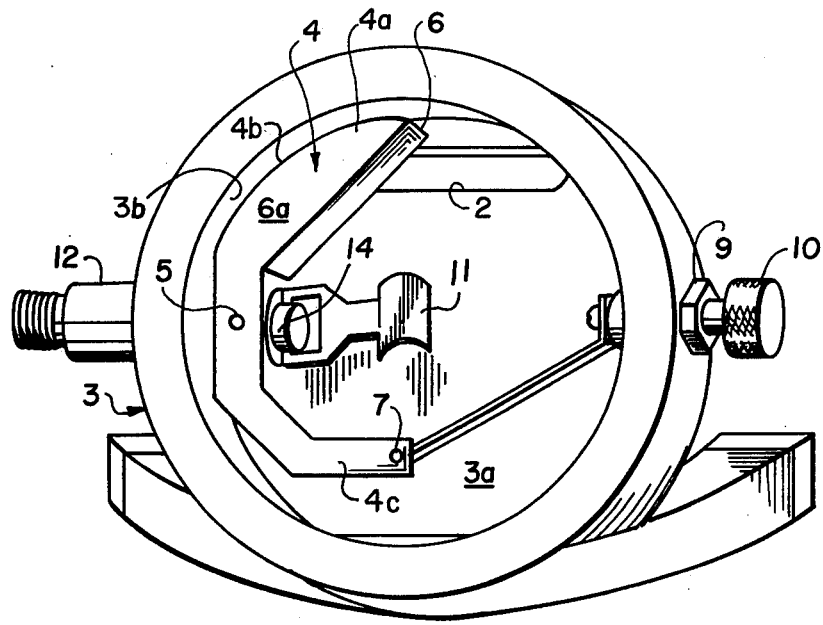
FIG. 1 is a perspective view of one embodiment of the invention mounted within an underwater breathing regulator having the diaphragm portion removed.

Referring to the drawings in particular the embodiment of the invention shown in the drawings comprises a cylindrical regulator housing generally designated 3, having in its cylindrical wall a compressed air inlet connection 12 which is supplied with compressed air from a source (not shown). The regulator has a circular back wall 3a in which there is a slotted inhalation port 2.

Figure 2:
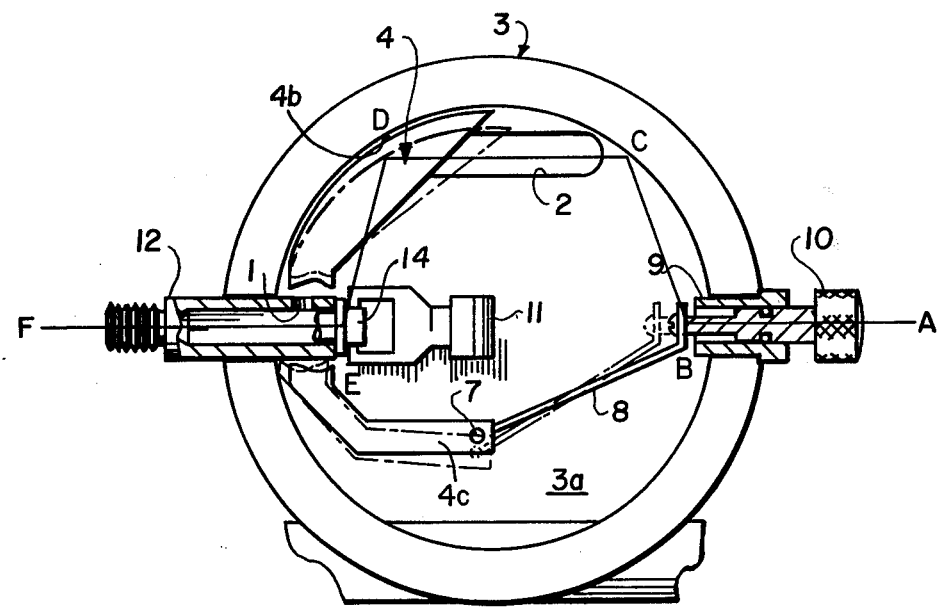
FIG. 2 is a partly in section frontal elevation of the invention in this embodiment.
Figure 3:
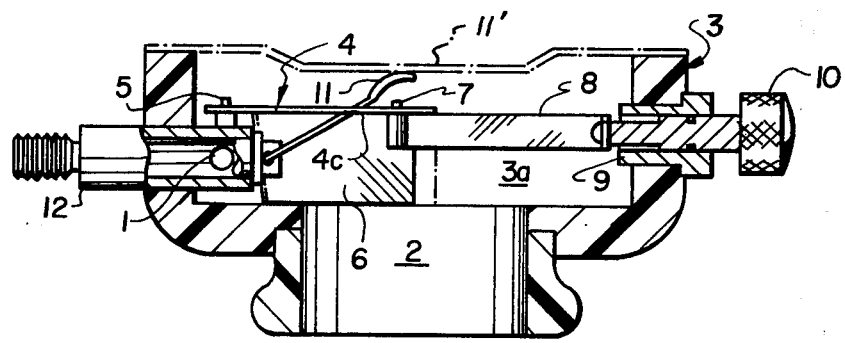
FIG. 3 is a partially in section elevation taken along the line ABCDEF in FIG. 2.

In accordance with the invention, a baffle plate generally designated 4, is pivotally mounted on pivot pin 5 which is rigidly fixed to the regulator housing 3. A section 4a of baffle 4 is provided with an edge 4b which conforms to the cylindrical wall 3b of the housing 3, and partially covers and is spaced away from inhalation port 2. Provided on its other edge is a baffle skirt 6 extending downward from a rear wall 6a toward the back wall 3a. A breathing gas flow space is defined by the walls 3a, 3b, 4b and 6. Baffle 4 includes an opposite lever portion 4c which is pivotally connected to a connecting rod 8 at a pivot point 7. The connecting rod 8 is connected with adjusting member or screw 10 which is threaded into fitting 9. Rotation of the screw 10 will cause its advancement or withdrawal in the fitting 9 to move the rod 8 and pivot arm 4c about pivot 5 thus causing edge 4a to move away from or toward inside wall 3b. As best shown in FIG. 2, an inlet port 1, supplied with air or a breathing gas mixture through connection 12, is situated so as to blow air into one end of the breathing gas flow space in the general direction of inhalation discharge port 2. The flow into port 1 is controlled by valve 14 which is actuated by lever 11 which in turn is actuated by a diaphragm 11, in FIG. 3. The air flow may be adjusted from a high speed direct flow from port 1 to port 2 when edge 4a is closely adjacent the inside wall 3b, to a slower less direct route when edge 4a is spaced away from inside wall 3b, in which latter case the air flow past edge 4a and baffle skirt 6 is deflected around the inside of the housing 3 eventually exiting through the inhalation discharge port 2. The location of baffle edge 4b is determined by the positioning of adjustment member 10 within its fitting 9.

While a specific embodiment of the invention has been shown and described in detail to illustrate the application of the principles of the invention, it will be understood that the invention may be embodied otherwise without departing from such principles.

What is claimed is:

1. A device for regulating the flow of breathing gas mixtures, comprising a rectangular housing having an interior cylyindrical wall and a circular back wall with an elongated slot formation therein forming an inhalation discharge port, an inlet port in said cylindrical wall for the inflow of breathing gas into said housing spaced apart from said discharge port, a double armed baffle pivotally mounted in said housing and pivotable on said circular back wall and having a first arm facing said back wall defining a breathing gas flow space between said baffle and said back wall and also having a portion covering a part of said inhalation discharge port and a second arm connected to said first arm, said inlet port being adjacent one end of said gas flow space and said discharge port being adjacent the opposite end and partially in communication with said gas flow space, adjusting means displaceably mounted on said housing wall and connected to said baffle second arm for positioning said baffle first arm relative to said interior cylindrical wall, said first arm being pivotable by said adjusting means toward said wall to reduce the flow space area and cause a major portion of the air flow from said inlet port to flow directly into the portion of said discharge port which is covered by said first arm, said first arm being pivotable away from said wall to increase the area of the flow space and allow the gas flow from the inlet port to pass the discharge port and to be deflected by said housing interior wall around the housing and thereafter to flow indirectly into the portion of said discharge port which is not covered by said first arm.

2. A device as in claim 1, wherein said baffle has a portion with an edge adjacent said inside wall and arcuately conforming to it, so as to define said flow space.

3. A device as in claim 1, wherein said baffle comprises a double armed lever including a first arm portion having said portion spaced from said circular back wall and an opposite lever portion, said adjusting means comprising a member threaded into said housing and connected to said lever portion.

4. A device as in claim 3, including an inlet valve at said inlet and lever means connected to said inlet valve for opening and closing it.

* * * * *